United States Patent
Mulvanerty

(10) Patent No.: US 8,128,973 B2
(45) Date of Patent: Mar. 6, 2012

(54) MEDICATED SKIN CARE PREPARATION FOR PROMOTING WOUND HEALING

(76) Inventor: Noreen Mulvanerty, Neponsit, NY (US)

( * ) Notice: Subject to any disclaimer, the term of this patent is extended or adjusted under 35 U.S.C. 154(b) by 638 days.

(21) Appl. No.: 12/066,206

(22) PCT Filed: Sep. 7, 2006

(86) PCT No.: PCT/US2006/034943
§ 371 (c)(1),
(2), (4) Date: Oct. 29, 2008

(87) PCT Pub. No.: WO2007/030666
PCT Pub. Date: Mar. 15, 2007

(65) Prior Publication Data
US 2009/0136435 A1    May 28, 2009

Related U.S. Application Data

(60) Provisional application No. 60/714,631, filed on Sep. 7, 2005.

(51) Int. Cl.
- A61K 36/68 (2006.01)
- A61K 36/28 (2006.01)
- A61K 36/73 (2006.01)
- A61K 36/00 (2006.01)

(52) U.S. Cl. ......... 424/738; 424/764; 424/765; 424/725

(58) Field of Classification Search ................. None
See application file for complete search history.

(56) References Cited

U.S. PATENT DOCUMENTS

| | | | |
|---|---|---|---|
| 5,997,876 A * | 12/1999 | Shikhashvili et al. | 424/730 |
| 6,576,269 B1 * | 6/2003 | Korneyev | 424/725 |
| 2002/0009472 A1 * | 1/2002 | Takekoshi et al. | 424/401 |
| 2004/0185123 A1 * | 9/2004 | Mazzio et al. | 424/730 |
| 2006/0008489 A1 * | 1/2006 | Egawa et al. | 424/401 |

* cited by examiner

Primary Examiner — Christopher R. Tate
(74) Attorney, Agent, or Firm — Dann, Dorfman, Herrell & Skillman; Kathleen D. Rigaut

(57) ABSTRACT

Herbal skin care compositions for the promotion of wound healing is provided.

5 Claims, No Drawings

MEDICATED SKIN CARE PREPARATION FOR PROMOTING WOUND HEALING

This application is a §371 application of PCT/US2006/034943, filed Sep. 7, 2006, which in turn claims priority under 35 U.S.C. §119(e) to U.S. Provisional Application No. 60/714,631, filed on Sep. 7, 2005. The entire disclosure of each of the foregoing applications being incorporated by reference herein as though set forth in full.

FIELD OF THE INVENTION

The present invention relates to skin care compositions. More specifically, the invention relates to herbal compositions comprising calendula, yarrow, wild rose, and plantain extracts and methods of use thereof.

BACKGROUND OF THE INVENTION

Several publications are cited throughout the specification in order to describe the state of the art to which this invention pertains. Each of these citations is incorporated herein by reference as though set forth in full.

Slow or improper wound healing may compromise the quality of life of an individual and/or lead to infection. Remedies, particularly herbal remedies, are desired by consumers for the promotion of rapid and proper wound healing.

SUMMARY OF THE INVENTION

In accordance with the present invention, a topical composition for promoting wound healing is provided, comprising at least two, preferably at least three, and more preferably all four extracts selected from the group consisting of calendula, yarrow, wild rose, and plantain extracts. In a particular embodiment, the topical composition comprises comprising about 30-70% calendula extract, about 10-30% yarrow extract, about 5-30% plantain extract, and about 5-30% wild rose extract. The topical compositions may also comprise at least one pharmaceutically acceptable carrier. The topical compositions may also comprise at least one agent selected from the group consisting of sunscreens, anti-aging agents, chemotherapeutic agents, chemopreventive agents, other wound-healing agents, anti-cellulite agents, pigment modulating agents, anti-irritation agents, steroids, anti-inflammatory agents, anti-fungal agents, anti-bacterial agents, moisturizing agents, emollients, anesthetics, anti-viral agents, vitamins, essential amino acids, coloring agents, fragrances, and essential fatty acids.

In accordance with another aspect of the instant invention, methods are provided for promoting wound healing by administering the topical compositions of the instant invention to a wound site.

DETAILED DESCRIPTION OF THE INVENTION

The topical compositions of the instant invention can be used to promote the healing of all superficial wounds of the skin and mucous membranes. For example, the composition may be applied directly to wound dressings, adhesive bandages, sutures, after suture care, on wounds, mild burns, insect bites, abrasions, cuts, and slow to heal wounds. The topical compositions may be applied by an applicator such as a wipe, swab, or roller.

The topical compositions of the instant invention may comprise medicinal plants which include the following constituents: triterpenoids which have anti-inflammatory activity that increase granulation at the site of the wound, promote metabolism of proteins and collagen, and help to grow new and healthy cells; styptics which help to stop bleeding; analgesics which minimize pain; anti-bacterial compounds which have broad coverage including both $Gram^+$ and $Gram^-$ bacteria; and anti-itch compounds.

The topical compositions of the instant invention comprise at least two, more preferably at least three, and most preferably all four extracts selected from the group consisting of calendula, yarrow, wild rose, and plantain extracts. In a preferred embodiment, the extracts are made from yarrow petals, leaves, and/or whole flowers; calendula petals and/or whole flowers; plantain leaves, and rose petals and/or whole flowers. Preferred ranges of the four extracts in the instant compositions are:

| | |
|---|---|
| calendula | about 30-70% |
| yarrow | about 10-30% |
| plantain | about 5-30% |
| wild rose | about 5-30% |

Two exemplary formulations are (1) calendula 60%, yarrow 20%, plantain 10%, and wild rose 10%; and (2) calendula 40%, yarrow 20%, plantain 20%, and wild rose 20%.

The extracts of the instant invention may be made with a menstruum comprising alcohol and water. Preferably, the menstruum comprises about 5-95% alcohol, more preferably about 30-70% alcohol, more preferably about 40-60% alcohol, and most preferably about 50% alcohol. The plant (herb): menstruum ratio for each can be about 1:0.2-20, more preferably about 1:1-5, more preferably about 1:2 (e.g., g:ml).

The topical compositions of the present invention may be made into a wide variety of product types such as, without limitation, liquids, lotions, powders, creams, salves, gels, milky lotions, sticks, sprays (e.g., pump spray), aerosols, ointments, pastes, mousses, dermal patches, controlled release devices, and other equivalent forms. Preferably, the compositions are in spray form. The topical compositions of the instant invention may comprise the extracts of the instant invention and at least one pharmaceutically acceptable carrier. "Pharmaceutically acceptable" refers to entities and compositions that are physiologically tolerable and do not typically produce an allergic or similar untoward reaction when administered to an animal, particularly a human. Pharmaceutically acceptable carriers are preferably approved by a regulatory agency of the Federal or a state government or listed in the U.S. Pharmacopeia or other generally recognized pharmacopeia for use in/on animals, and more particularly in/on humans. A "carrier" refers to, for example, a diluent, adjuvant, excipient, auxiliary agent or vehicle with which an active agent of the present invention is administered. Such pharmaceutically acceptable carriers can be sterile liquids, such as water (may be deionized), alcohol (e.g., ethanol, isopropanol), oils (including those of petroleum, animal, vegetable or synthetic origin, such as peanut oil, soybean oil, mineral oil, sesame oil and the like), and other organic compounds or copolymers. Water or aqueous saline solutions and aqueous dextrose and glycerol solutions may also be employed as carriers. Suitable pharmaceutical carriers and other agents of the compositions of the instant invention are described in "Remington's Pharmaceutical Sciences" by E. W. Martin (Mack Pub. Co., Easton, Pa.) and "Remington: The Science And Practice Of Pharmacy" by Alfonso R. Gennaro (Lippincott Williams & Wilkins, 2005). Additional general types of pharmaceutically acceptable topical carriers include, without limitation, emulsions (e.g., microemulsions and nanoemulsions), gels (e.g., an aqueous, alcohol, alcohol/water, or oil (e.g., mineral oil) gel using at least one suitable gelling agent (e.g., natural gums, acrylic acid and acrylate polymers and copolymers, cellulose derivatives (e.g., hydroxymethyl cellulose and hydroxypropyl cellulose), and hydrogenated butylene/ethylene/styrene and hydrogenated ethylene/propylene/styrene copolymers), solids (e.g., a wax-based stick, soap bar composition, or powder (e.g., bases such as talc, lactose, starch, and the like), and liposomes (e.g., unilamellar, multilamellar, and paucilamellar liposomes, optionally containing phospholipids). The pharmaceutically acceptable carriers also include stabilizers, penetration enhancers (see, e.g., Remington's cited below), chelating agents (e.g., EDTA, EDTA derivatives (e.g., disodium EDTA and dipotassium EDTA), iniferine, lactoferrin, and citric acid), and excipients.

In yet another embodiment, the compositions of the invention may further comprise at least one additional therapeutic agent. The therapeutic agents, which may optionally be herbal, include, without limitation, sunscreens (e.g., organic or inorganic sunscreens such as cinnamate compounds (e.g., methoxyoctylcinnamate), titanium dioxide, zinc oxide, iron oxide, zirconium oxide, p-aminobenzoic acid, anthranilates, salicylate esters, dihydroxycinnamic acids, trihydroxy-cinnamic acids, diphenylbutadiene, stilbene, dibenzalacetone, benzalacetophenone, naphtholsulfonates, di-hydroxynaphthoic acids, o- and p-hydroxybiphenyldisulfonates, coumarin derivatives, diazoles, quinine salts, quinoline derivatives, hydroxy- or methoxy-substituted benzophenones, uric and violuric acids, tannic acids, hydroquinone, benzophenones, and derivatives and salts thereof), anti-aging agents (sunscreens, anti-oxidants (e.g., vitamins such as ascorbic acid, vitamin B, biotin, pantothenic acid, vitamin D, vitamin E and vitamin C), sodium bisulfite, yeast extract, gingko biloba, bisabolol, panthenol, alpha hydroxy acids, and oligosaccharides (e.g., melibiose)), chemotherapeutic and/or chemopreventative agents (e.g., placitaxel, cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives), steroids, anti-inflammatory agents (e.g., steroidal (e.g., corticosteroids (e.g., hydrocortisone), hydroxyltriamcinolone, alpha-methyl dexamethasone, dexamethasone-phosphate, beclomethasone dipropionate, clobetasol valerate, desonide, desoxycorticosterone acetate, dexamethoasone, dichlorisone, deflorasonediacetate, diflucortolone valerate, fluadronolone, fluclarolone acetonide, fludrocortisone, flumethasone pivalate, fluosinolone acetonide, fluocinonide, flucortine butylester, fluocortolone, fluprednidene (flupredylidene) acetate, flurandronolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone and its esters, chloroprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, and triamcinolone) and non-steroidal anti-inflammatory agents (e.g., salicylates, acetic acid derivatives, fenamates, propionic acid derivatives and pyrazoles)), pigment modulating agents (e.g., depigmenting agents such as lipoic acid, arbutim, dihydrolipoic acid, resveratrol, ascorbic acid, kojic acid, hydroquinone, isoflavones, retinoids (e.g., retinol, retinoic acid, and retinyl palmitate), tyrosinase inhibitors, melanosome transfer inhibitors, selective cytotoxic agents for melanocytes, and natural extracts (e.g., licorice extract, gatuline A (pilewort extract), and micromerol (butylene glycol and apple extract))), exfoliating agents (e.g., organic hydroxy acids (e.g., alpha and beta hydroxy acids), salicylic acid, glycolic acid, lactic acid, 5-octanoyl salicylic acid, hydroxyoctanoic acid, hydroxycaprylic acid, lanolin fatty acids, sulphydryl compounds, protease or peptase enzymes (natural and bio-engineered), mimetic compounds that mimic hydroxyl acids, and bioactive metals (e.g., manganese, tin, and copper), and natural soy-based products), other wound-healing agents (e.g., nitric oxide, aminoxyls, furoxans, nitrosothiols, nitrates, anthocyanins, nucleosides such as adenosine, nucleotides such as ADP and ATP, neurotransmitter/neuromodulators (e.g., acetylcholine and 5-hydroxytryptamine), histamine, catecholamines (e.g., adrenalin and noradrenaline), lipid molecules (e.g., sphingosine-1-phosphate and lysophosphatidic acid), amino acids (e.g., arginine and lysine), vitamin A, vitamin D, bradylinins, substance P, calcium gene-related peptide (CGRP), insulin, vascular endothelial growth factor (VEGF), thrombin, antibodies to platelet endothelial cells surface marker, compounds specifically binding adhesion molecules (e.g., ICAMs, NCAMs, PECAMs), extra-cellular matrix proteins (e.g., glycosaminoglycans), fibrous proteins (e.g., collagen; elastin, fibronectins, and laminin), growth factors (e.g., platelet derived growth factors (PDGF), epidermal growth factor (EGF), keratinocyte growth factor (KGF), vascular endothelial growth factors (VEGFs), fibroblast growth factors (FGFs), transforming growth factors (TGFs), and insulin-like growth factor-1 (IGF-1)) tumor necrosis factor-alpha (TNF-alpha), tumor necrosis factor-beta (TNF-beta), and thymosin B4), anti-irritation agents (e.g., methyl nicotinate, corticosteroids, ascorbic acid, and acetic acid), anti-cellulite agents (e.g., xanthine compounds such as caffeine, theophylline, theobromine, and aminophylline), anti-fungal agents (e.g., terbinafine hydrochloride, nystatin, amphotericin B, griseofulvin, ketoconazole, miconazole nitrate, flucytosine, fluconazole, itraconazole, clotrimazole, benzoic acid, salicylic acid, and selenium sulfide), anti-bacterial agents (e.g., antibiotics, penicillins, cephalosporins, carbacephems, cephamycins, carbapenems, monobactams, aminoglycosides, glycopeptides, quinolones, tetracyclines, macrolides, fluoroquinolones, and derivatives thereof), moisturizing agents (e.g., polyhydric alcohols (e.g., glycerin, propylene glycol, 1,3-butyleneglycol, polyethylene glycol, sorbitol, isoprene glycol, and POB methyl glucoside), saccharides (e.g., trehalose, pullulan, and maltose), and biological polymers (e.g., sodium hyaluronate, chondroitin sodium sulfate, collagen, elastin, amino acids, sodium lactate, pyrrolidone sodium carboxylate, and urea), emollients (e.g., lanolin, spermaceti, mineral oil, paraffin, petrolatum, white ointment, white petroleum, yellow ointment, vegetable oils, waxes, cetyl alcohol, glycerin, hydrophilic petrolatum, isopropyl myristate, myristyl alcohol, and oleyl alcohol), antioxidants (e.g., water-soluble antioxidants (e.g., sulfhydryl compounds, sulfhydryl derivatives (e.g., sodium metabisulfite and N-acetyl-cysteine), lipoic acid, dihydrolipoic acid, resveratrol, acetyl-cysteine (iniferine), lactoferrin, ascorbic acid, and ascorbic acid derivatives (e.g., ascorbyl palmitate and ascorbyl polypeptide)), oil-soluble antioxidants (butylated hydroxytoluene, retinoids (e.g., retinol and retinyl palmitate), tocopherols (e.g., tocopherol acetate), tocotrienols, and ubiquinone), and natural extracts (e.g., extracts containing resveratrol, flavonoids and isoflavonoids and derivatives thereof (e.g., genistein and diadzein) such as grape seed, green tea, pine bark, propolis, and legume extracts), anti-swelling agents (e.g., lanolin, aloe vera extract, hydrocortisone, and menthol), anesthetics (e.g., ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecgonidine, ecogonine, etidocaine, euprocin, fenalcomine, fomocaine, hexylcaine, hydroxytetracaine, isobutyl p-aminobenzoate, ketamine, leucinocaine, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and pharmaceutically acceptable salts thereof), and anti-viral agents (e.g., amantadine hydrochloride, rimantadine, acyclovir, famciclovir, foscamet, ganciclovir sodium, idoxuridine, ribavirin, sorivudine, trifluridine, valacyclovir, vidarabine, didanosine, stavudine, zalcitabine, zidovudine, interferon alpha, and edoxudine). The compositions may also comprise cosmetic agents such as coloring agents and fragrances. The composition may also comprise at least one nutrient, such as vitamins (e.g., vitamin A, vitamin B, vitamin C, and vitamin E), essential amino acids, and essential fatty acids. In a particular embodiment, the topical compositions comprise at least one agent selected from the group consisting of anti-fungal agents, anti-bacterial agents, anesthetics, and anti-viral agents.

Protocols and procedures which facilitate formulation of the topical compositions of the invention can be found, for example, in Cosmetic Bench Reference 2005, Published by Cosmetics & Toiletries, Allured Publishing Corporation, Illinois, USA, 2005 and in *International cosmetic ingredient dictionary and handbook*. 10th ed. Edited by Tatra E. Gottschalck and Gerald E. McEwen. Washington, Cosmetic, Toiletry and Fragrance Association, 2004 each of the foregoing references being incorporated herein by reference.

The formulations of the invention may be applied to wounds to promote healing. The wound surface may be treated up to about five times a day and is more preferably treated about two times a day. Progress of wound healing may be monitored using a variety of techniques, including visual inspection.

Toxicity and therapeutic efficacy of the particular formulas described herein can be determined by standard pharmaceutical procedures such as, without limitation, in vitro, in cell cultures, ex vivo, in the chick chorioallantoic membrane (CAM) ex vivo model system, or on experimental animals. The data obtained from these studies can be used in formulating a range of dosage for use in human. The dosage may vary depending upon form and route of administration. Dosage amount and interval may be adjusted individually to levels of the active ingredient which are sufficient to, for example, induce wound healing (i.e., a therapeutically effective amount). Factors to be considered for dosage amount include, without limitation, the subject being treated, the severity of the wound, the manner of administration, and the judgment of the prescribing physician. Depending on the severity and responsiveness of the wound to be treated, dosing can be of a single or a plurality of administrations, with course of treatment lasting, for example, from a day to several weeks or until diminution of wound is achieved.

The following example is provided to illustrate certain embodiments of the invention. They are not intended to limit the invention in any way.

Example

Plants contained in Omyst were grown on an organic farm in Warwick, N.Y. Each plant was steeped in a liquid menstruum (50% alcohol and 50% water (50A:50W; 100 proof)), thereby infusing the liquid with the active constituents of the herb. The tincture then became a stable solution that is preserved against deterioration for an indefinite length of time.

The herb:menstruum ratio compares the weight of the herb to the volume of the total liquid menstruum. Each of the plants/herbs used are fresh, therefore the tincture can be 1:2 (1 part in gram of fresh herb combined with 2 parts in milliliters of menstrual to make the extract). For example, 0.5 ounce of each fresh herb to 1 ounce of 50A:50W or 64 ounces of fresh herbs to 128 ounces (one gallon) of 100 proof alcohol (50A:50W) may be used.

Quart sized ball jars were sterilized and then filled with leaves and petals at the desired ratio. The jars are then filled with alcohol and then sealed airtight. The composition was then left in a cool, dry dark space for 6 weeks.

Alternatively the tinctures may be prepared in one gallon amber glass bottles. The tinctures may then be, optionally, subjected to settling and filtering stages. The tincture may then be divided according to percentages into one ounce aluminum atomizer spray bottles under strict aseptic technique.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A topical composition comprising about 60% calendula extract, about 20% yarrow extract, about 10% plantain extract, and about 10% wild rose extract.

2. The composition of claim 1 further comprising at least one pharmaceutically acceptable carrier.

3. The composition of claim 1, further comprising at least one agent selected from the group consisting of sunscreens, anti-aging agents, chemotherapeutic agents, chemopreventive agents, other wound-healing agents, anti-cellulite agents, pigment modulating agents, anti-irritation agents, steroids, anti-inflammatory agents, anti-fungal agents, anti-bacterial agents, moisturizing agents, emollients, anesthetics, anti-viral agents, vitamins, essential amino acids, coloring agents, fragrances, and essential fatty acids.

4. The composition of claim 1, further comprising at least one agent selected from the group consisting of anti-fungal agents, anti-bacterial agents, anesthetics, and anti-viral agents.

5. A method of promoting wound healing comprising administering the composition of claim 1 to the wound site.

* * * * *